United States Patent [19]

Lin et al.

[11] Patent Number: 5,644,501
[45] Date of Patent: Jul. 1, 1997

[54] METHOD OF USING A COMPUTER TO COLLECT CHEMICAL SIGNALS DIRECTLY

[76] Inventors: Shengfu Lin, 3F, 7, Lane 110, Chien-Kang Street, Tapei, Taiwan; Chih-I Lin, 14292 Spring Vista La., Chino Hills, Calif. 91709

[21] Appl. No.: 354,031

[22] Filed: Dec. 6, 1994

[51] Int. Cl.⁶ .................................................. G01N 27/26
[52] U.S. Cl. ........................ 364/496; 364/497; 364/498; 364/499; 204/407; 204/400; 204/406
[58] Field of Search ..................................... 364/496–500, 364/550, 551.01, 509, 510, 413.08, 413.09, 413.11, 413.12; 204/400, 401, 409, 405–407; 422/68.1, 81, 82.01, 82.02, 62, 119; 340/632; 324/464, 468, 465, 438; 128/734, 738

[56] References Cited

U.S. PATENT DOCUMENTS

| | | |
|---|---|---|
| 4,743,954 | 5/1988 | Brown ........................................ 357/25 |
| 5,197,017 | 3/1993 | Caroll et al. ........................... 364/413.09 |
| 5,198,771 | 3/1993 | Fidler et al. .............................. 324/438 |
| 5,198,774 | 3/1993 | Williams, II et al. ..................... 324/468 |
| 5,298,145 | 3/1994 | Garraway et al. ......................... 204/406 |
| 5,372,141 | 12/1994 | Gallup et al. ............................. 128/734 |
| 5,374,892 | 12/1994 | Sturrock et al. .......................... 204/407 |
| 5,438,271 | 8/1995 | White et al. .............................. 204/406 |
| 5,470,484 | 11/1995 | McNeel ................................... 422/82.01 |

Primary Examiner—Emanuel T. Voeltz
Assistant Examiner—Hal D. Wachsman
Attorney, Agent, or Firm—Bacon & Thomas

[57] ABSTRACT

The present invention relates to a method of using a computer to collect chemical signals directly from a chemical sensor. This method first transforms analog chemical signals received from the chemical sensor into analog electronic signals in a transforming circuit in cooperation with control computer programs executed in the computer, then uses an Analog-to-Digital converter, which connects the transforming circuit with the computer, to transform the analog electronic signals into digital signals; and finally transfers the digital signals to the computer.

4 Claims, 4 Drawing Sheets

METHOD OF USING A COMPUTER TO COLLECT CHEMICAL SIGNALS DIRECTLY

FIELD OF THE INVENTION

The present invention is related to a method of using a computer to collect chemical signals directly.

BACKGROUND OF THE INVENTION

There are three types of chemical sensors: chemical sensors used in conductometry, chemical sensors used in amperometry and chemical sensors used in potentiometry. For example: pH electrodes, ion-selective electrodes, ISFET (ion-selective field effect transistors), enzyme electrodes, biosensors, etc. are widely used in chemical, biochemical, biotechnological, environmental protection and medical analyzers such as a: pH-meter, ion analyzer, polarography, chemical analyzer, bioanalyzer, bioreactor, ion chromatography, flow-injection analyzer, etc. Moreover, Chemical sensors are used in quality control analysis, on-line analysis and monitor-control apparatus for chemical manufacturing processes. U.S. Pat. No. 4,897,128 discloses a method of controlling the ionic concentrations of reactants in a zinc phosphate coating sink by using pH-electrodes and fluorine-ion selective electrodes.

A chemical sensor can convert a specific chemical signal (i.e. concentration of a certain component of a sample) or the sum of many chemical signals into an electronic signal such as electric potential, resistance, or current. However, in order for the users to understand the physical meanings of a chemical signal, this electronic signal still needs to be further processed, stored, and/or displayed by an signal processing equipment. For example, a pH-electrode has to be incorporated with a pH meter to determine the pH value of a solution. Similar requirement applies to the usage of a chemical analyzer, and pH monitor-control equipment. A chemical sensor for amperometry can determine the reaction current in the potential static condition by relying on a potentiostat, and then indirectly obtain the concentration of a specific specie. Similar requirement applies to the usage of a chemical analyzer and a biochemical analyzer. A chemical sensor for conductometry can determine the conductivity by relying on a conductometer, and the determined conductivity can then be used to indicate the ending of a conductometric titration, or used as the standards of ionic concentrations in ion chromatography. Each of these kinds of signal processing equipment has a specific usage, and cannot be exchanged for use in another chemical sensor. For example, a pH-meter can not be without a conductometer or a coulometer, and it also can not be extended to another use without a special design, a potentiometer cannot be extended to be used in potentiostatic coulometry.

Generally speaking, conventional signal processing equipment can be divided into 4 categories. The first category includes the simple instruments which cannot be connected to a computer or a recorder. For example, pH-meters (types 704, 620, 588) of Metrohm, Switzerland, do not have very powerful functions, and do not have the ability to execute data communication with other instruments like chemical analyzers.

The second type of signal processing equipment, however cannot be connected with a computer externally but, is able to communicate with an external recorder through its analog signal output node, and, therefore, enhance its function. Examples are the pH-meter (PHM82) of Radiometer, Denmark and the, Potentio/Galvanostat and Coulomb/Amperohour Meter of Nichia, Japan. The functions of these signal processing equipment are still limited. Although an analog signal output node is available, it is still physically difficult to execute data communication with other instruments.

The third type of signal processing equipment cannot be externally connected with either a computer or a recorder but, has its own built-in display and printer. Examples are the modular biological fluid analyzer disclosed in U.S. Pat. No. Des. 330,770, and a clinical chemistry analyzer disclosed in U.S. Pat. No. Des. 332,314. These built-in functions clearly can not be compared with those of a computer. For example, the resolution of a computer monitor is better than a built-in display of a signal processing equipment. A computer also has superior data processing/storing capabilities and various accessories which can be mounted into the computer easily. Moreover, the analyses and data processing functions of this type of signal processing instruments cannot be extended or enhanced.

The fourth type of signal processing equipment can be connected with a computer externally in order to enhance its data processing/storing/display ability. Example include the voltammetry Model 693 VA Processor from Metrohm, Switzerland; the PHM 85 pH-meter from Radiometer, Denmark; the Potentiostat/Galvanostat Model 273A from EG&G, U.S.A.; a chemical analyzer disclosed in U.S. Pat. No. 4,935,875; and the on-line biological inhibition/toxicity detector disclosed in U.S. Pat. No. 5,106,511. This type of signal processing equipment contains a central processing unit. For example, line 17, column 5 of U.S. Pat. No. 5,106,511 and line 45, column 6 of U.S. Pat. No. 4,935,875 state that these signal processing equipment use a Model 6809 microprocessor (Motorola, U.S.A.), ROM, RAM, timer, display or monitor, keyboard or I/O port, ADC, etc. (For further details, please refer to FIG. 1 of U.S. Pat. No. 4,935,875 and its explanation.) In addition, when these signal processing equipment are to be connected externally with computers, RS-232 or GPIB cards needs to be Used as the medium for data communication.

In order to extend the analysis and data processing functions, the inventors have focused their research on the structure of the fourth type of signal processing equipment. The result is that except for some minor components such as ADC, the primary components such as CPU, ROM, RAM, timer, monitor, keyboard, I/O port, printer and disk drive, are all included in a computer. This is advantageous because the primary components of a computer are generally more powerful and more compatible to external accessories than the built-in components in the fourth type of signal processing equipment. Therefore, the fourth type of signal processing equipment may essentially be replaced by a computer. In addition, the minor-components such as ADC can be easily purchased in the market. Accordingly, it is possible to use an ADC bought from the market to directly convert the analog signals from a chemical sensor into digital signals, and transfer the digital signals to a computer where they are processed. If this can be accomplished, the signal processing equipment used at the present time can be entirely replaced by a computer with modifications. Nowadays, some mechanical sensors or thermal sensors are using the same idea of replacing signal processing equipment with computers and ADCs. However, this idea has not been used in chemical sensors.

Based on the above analyses, the inventors used a market-purchased ADC to connect a chemical sensor (i.e. a pH electrode) and a computer. In other words, the output signals from a chemical sensor were received in a series as follows:

"chemical sensor→ADC→computer". However, the results showed that although a large number of data were collected, the average value of these data could not represent the actual value accurately because the average values were not consistent for several runs repeated by the same procedures. The deviations were large and no pattern could be found.

After more intensive research, the inventors found out that the addition of a voltage follower could solve the existing problem. That is to say, if the connection is in a series of "chemical sensor→voltage follower→ADC→computer", the output signals of a chemical sensor can be easily and accurately obtained.

Furthermore, current ADCs in the market often have an additional function of Digital-to-Analog Conversion (DAC) at the same time. Therefore, it is theoretically possible to use a DAC to convert the digital signals sent by a computer into analog signals, and therefore use a chemical sensor to execute voltammetry applications; or under potentiostat conditions, to execute amperometry and obtain a concentration of a certain component of a sample. The actual experimental results showed that although the voltage output of the DAC was stationary, the electric potential of the working electrode was fluctuating. However, this problem can be solved by the addition of a potentiostat circuit. Similarly, a potentiostat circuit can be used to solve the same problem in potentiometry under galvanostat conditions.

In the conventional signal processing equipment of a chemical sensor for conductometry, a transducer has to be added to reduce the voltage of an alternating current source for the conductance cell. However, the inventors found that by executing a control program in the computer, the DAC can be used as an alternating current source.

Based on these three discoveries, a system containing a computer, an ADC/DAC, a potentiostat circuit, a voltage follower and a proper computer program which can be executed in said computer can be used to carry out amperometry, potentiometry, conductometry, and voltammetry for different chemical sensors. In other words the invention provides a method and system having the combined functions of a potentiometer, a pH meter, an amperometer, a conductometer, a potentiostat, a Galvanostat, a voltammetric processor, and thereby substantially covers all the equipment which use chemical sensors or any extension uses of these equipment, e.g. as a conductometer used in ion-chromatography. In contrary, the conventional signal processing equipment for chemical sensors have their own specific usages that cannot be exchanged. For example, a pH meter can be used only as a pH meter, not a potentiostat, and a voltammetric processor can not be used as a conductometer at the same time.

In addition, because ADC/DAC cards on the market usually have DIO (digital input/output) functions, and hence they can also be used as the control of a pump or a valve, the system described above can generally be connected with other accessories (if necessary) to be used as a chemical analyzer, bio-chemical analyzer, clinic analyzer, pH/electric potential/conductance automatic titration meter, ion chromatography, polarography, and a quality control, on-line analysis and monitor-control equipment of a chemical manufacturing process.

SUMMARY OF THE INVENTION

The first objective of this invention is to provide a transforming circuit and a control computer program in cooperation with a chemical sensor, an ADC and a computer to convert chemical signals into electronic digital signals, and then transfer the electronic digital signals to the computer.

The second objective of this invention is to provide a system for collecting chemical signals from a chemical sensor, which includes a computer, an ADC, a transforming circuit and a proper computer program which can be executed in said computer.

The third objective of this invention is to provide a system for collecting chemical signals from a chemical sensor, which includes a computer, ADC/DAC/DIO interface cards, a transforming circuit and a proper computer program which can be executed in the computer.

In order to accomplish these objectives, a method of using a computer to collect chemical signals directly from a chemical sensor is disclosed herein. This method comprises the followings steps: transforming analog chemical signals received from the chemical sensor into analog electronic signals in a transforming circuit in cooperation with a control computer program executed in a computer; transforming the analog electronic signals into digital signals by using an Analog-to-Digital converter (ADC) which connects the transforming circuit with the computer; and transferring the digital signals from the Analog-to-Digital converter to the computer.

The present invention also provides a system for collecting chemical signals from a chemical sensor including:

a computer;

one or more ADC interface cards which are connected with the computer and;

one or more transforming circuits, one end of the one or more transforming circuits being connected with the chemical sensor, and the other end of the said one or more transforming circuits being connected with the one or more ADC interface cards.

DETAILED DESCRIPTION OF THE INVENTION

Figure 1:
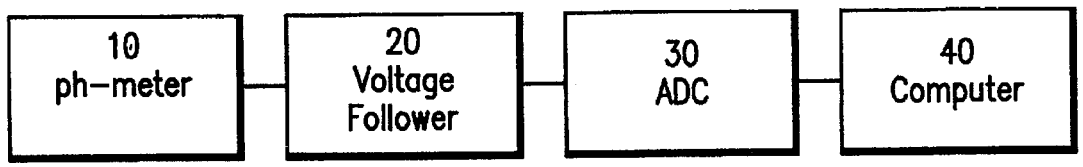
FIG. 1 is a block diagram which shows a system for collecting chemical signals from a chemical sensor according to a first preferred embodiment of the present invention.

The present invention is related to a method of using a computer to collect chemical signals directly from a chemical sensor. This method includes the followings steps: transforming analog chemical signals received from the chemical sensor into analog electronic signals in a transforming circuit in cooperation with a control computer program executed in a computer; transforming the analog electronic signals into digital signals by using an Analog-to-Digital converter which connects the transforming circuit with the computer; and transferring the digital signals from the Analog-to-Digital converter to the computer.

The chemical sensor can be also a sensor array. In Chapter 6 entitled "Multi-Component analysis in Chemical Sensing", Vol. 2 entitled "Chemical and Biochemical Sensors", of *Sensors* (edited by W. Gopel, I. Hesse and J. N. Zemel, and published by VCH company, Germany), a signal sensor, a sensor array, and the combination of both are demonstrated. The chemical sensors described here are the general chemical sensors, including the common biosensors, biochemical sensors, enzyme electrodes, gas sensors, etc. The form of these chemical sensors can be a probe, an electrochemical sensor, a liquid electrolyte sensor, a solid state electrochemical sensor, a field effect chemical sensor, a calorimetric chemical sensor, an optochemical sensor, a piezoelectrically chemical sensor, etc. These sensors are described in Chapters 1, 5, 7, 8, 9, 10, 11, 12, 13, 14 and 16, Vols. 2 and 3 of *Sensors* (edited by W. Gopel, I. Hesse and J. N. Zemel, and published by VCH company, Germany), and are of the type which can convert chemical signals into electronic signals.

The transforming circuit can be a voltage follower, a current—potential converter, a potentiostat circuit, a galvanostat circuit, or a combination thereof.

The voltage follower described above is a known circuit. Please refer to *Microelectronics*, Jacob Millman and Arvin Garbel, second edition, p. 445. This voltage follower is used in this invention to convert the high impedance electronic signals of the chemical sensors described above to medium or low impedance signals. Generally, the output electronic signals of a chemical sensor are high impedance electronic signals of about $10^5$–$10^6$ Ohms. If these signals are connected with an ADC directly, the ADC cannot convert the analog signals into digital signals accurately. However, if a voltage follower is inserted between the chemical sensor and an ADC, the problem will be solved.

The current-potential converter is a known circuit. Please refer to *Microelectronics*, Jacob Millman and Arvin Garbel, second edition, pp. 449–450. This current-potential converter can convert the electric current signals of a chemical sensor used in amperometry into voltage signals, in order for the ADC to convert the analog voltage signals into digital signals.

The potentiostat circuit a known circuit. Please refer to *Principles of Instrumental Analysis*, Douglas A. Skoog, p. 49. This potentiostat circuit can equalize the electric potential output of a DAC and the voltage of the working electrode of the chemical sensor. In other words, the voltage of the working electrode is constant. If the DAC is connected to a chemical sensor, the voltage output of the DAC, V, and the voltage of the working electrode of the chemical sensor, $V_1$, has the following relationship:

$$V=V_1+V_2+IR+V_3+V_4$$

$V_1$ stands for the voltage of the counter electrode, IR stands for the IR drop caused by current—resistance, and $V_3$ and $V_4$ are the overvoltage of the working electrode and counter electrode, respectively. Because $V_3$, $V_4$ are related to the complex kinetic polarization and concentration polarization, the voltage of the working electrode is not stable even though the DAC output voltage (V) is constant. During an electro-chemical analysis, it is required that the voltage of the working electrode remains constant. Therefore, a potentiostat circuit has to be inserted between the DAC and the chemical sensor to solve the problem.

Each of the voltage follower, current—potential converter, potentiostat and/or galvanostat circuits described above is a simple circuit. When necessary, they can be combined to be in one circuit board, or even made into a computer serial port card, or be included in an ADC interface card. The ADC described above is a known circuit. Some ADC interface cards on the market have DAC, and DIO functions in one interface card. For example, the PCL-718, PCL-818, PCL-812, PCL-812PG interface cards manufactured by Advantech Co. Ltd., Taiwan all have 16 channels ADC, 16 DI (digital inputs), 16 DO (digital outputs) and 1–2 channels DAC. In each of these ADC interface cards described above, the DAC and/or DIO channels can also be formed in a separate interface card.

The computer described above can be a desktop computer (a PC or a minicomputer), or a portable computer (notebook or laptop computer), preferably a desktop PC or a notebook computer.

The control computer program can be stored as a firmware or software which can be read and executed by the computer, and preferably as a software due to software's flexibility of editing and change.

When necessary, a galvanostat circuit can be inserted between the DAC and the chemical sensor to conform to the galvanostat requirement in electric potential measurement during a galvanostat electrolysis. This Galvanostat circuit is a known circuit and is described in *Principles of Instrumental Analysis*, Dougls A. Skoog, third edition, p. 49.

A system for collecting chemical signals disclosed by the present invention includes:

a computer;

one or more chemical sensors;

one or more ADC interface cards which are connected with the computer; and one or more transforming circuits, one end of the one or more transforming circuits being connected with the one or more chemical sensors, and the other end of the one or more transforming circuits being connected with the one or more ADC interface cards.

The transforming circuit can be a voltage follower, or a current-potential converter and a potentiostat circuit. Additionally, a galvanostat circuit can be included in the transforming circuit.

The function of this system entirely depends on a control computer program executed by the computer.

The computer, ADC interface card, chemical sensor, voltage follower, current-potential converter, potentiostat circuit and galvanostat circuit contained in the system are the same as those described above in connection with method of using a computer to collect chemical signals from a chemical sensor directly.

The one or more ADC interface cards can be connected with the computer by inserting gold contacts provided on one or more ADC interface cards into one or more slots provided by the computer or expanded therefrom.

Preferably, the one or more ADC interface cards can further have digital-to-analog converter (DAC) and digital input/output (DIO) functions.

Generally, the system described above can be connected with other accessories (if necessary) to be used as a chemical analyzer, bio-chemical analyzer, clinic analyzer, pH/electric potential/conductance automatic titration meter, ion chromatography, polarography, and a quality control, on-line analysis and monitor-control equipment of a chemical manufacturing process.

This invention further provides a system for collecting chemical signals including;

a computer;

one or more chemical sensors;

one or more ADC/DAC interface cards which are connected with the computer;

a transforming circuit, one end of the transforming circuit being connected with the one or more chemical sensors, and the other end of the transforming circuit being connected with the one or more ADC/DAC interface cards, wherein the transforming circuit is a voltage follower, or a current-potential converter and a potentiostat circuit. Additionally, a galvanostat circuit can be included in the transforming circuit.

The function of this system entirely depends on the control computer program executed by the computer.

The computer, ADC/DAC interface card, chemical sensor, voltage follower, current-potential converter, potentiostat circuit and galvanostat circuit contained in the system are the same as those described above in in connection with the method of using a computer to collect chemical signals from a chemical sensor directly.

The one or more ADC/DAC interface cards can be connected with the computer by inserting gold contacts provided on the one or more ADC interface cards into one or more slots provided by the computer or expanded therefrom.

Preferably, the one or more ADC/DAC interface cards can further have a digital input/output (DIO) function.

To further explain this invention, several preferred embodiments will be described in the following text by referring to the accompanying figures.

FIG. 1 is a block diagram which shows a system for collecting chemical signals from a chemical sensor according to a first preferred embodiment of the present invention, wherein 10 represents the chemical sensor, 20 is a voltage follower, 30 is ADC, and 40 is a computer.

Figure 2:
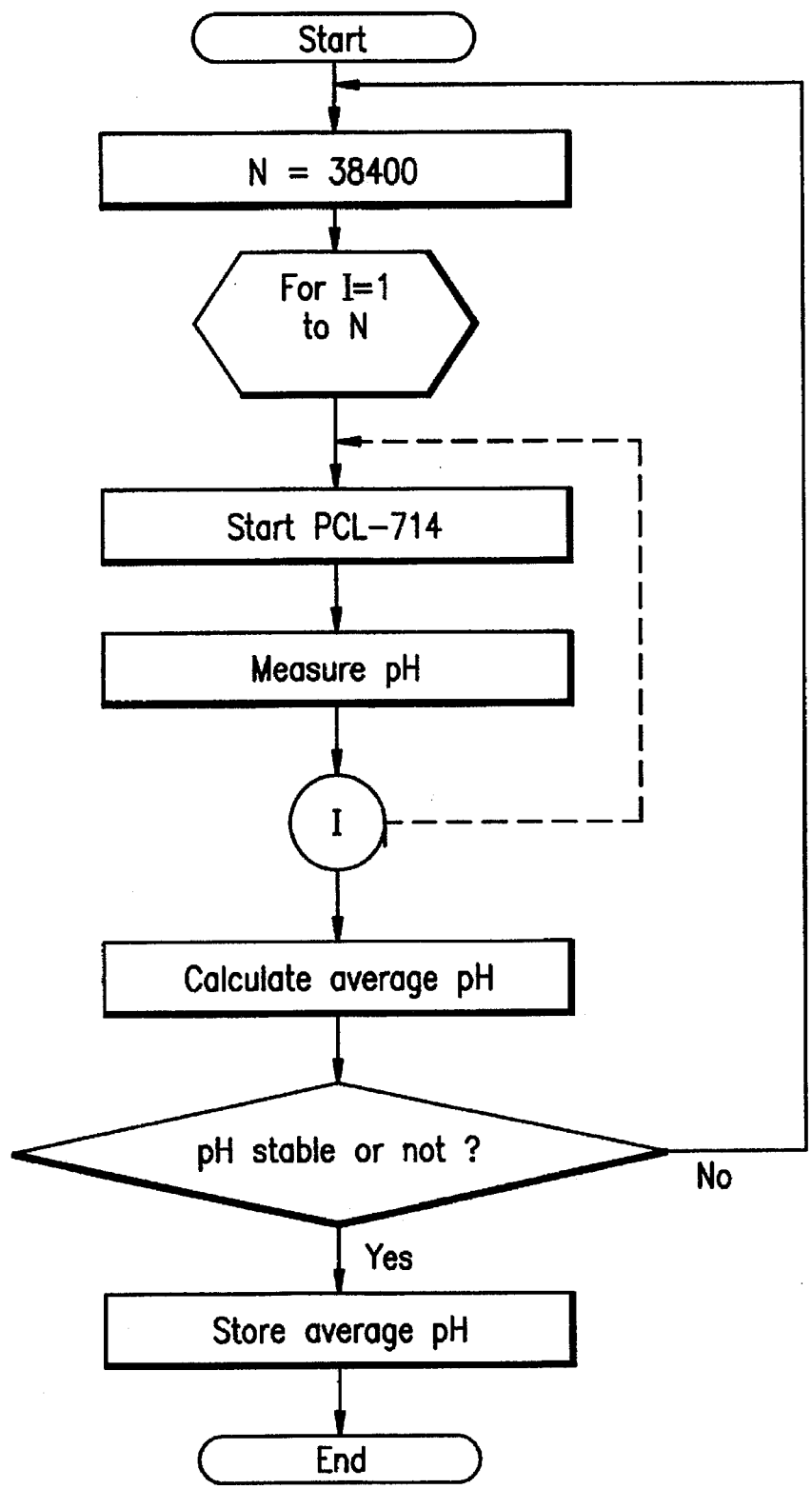
FIG. 2 is a flow chart of a control computer program to be executed in the computer in FIG. 1 when the chemical sensor thereof is a pH meter.

FIG. 2 is a flow chart of a control computer program to be executed in the computer of FIG. 1 when the chemical sensor thereof is a pH meter, in which the ADC/DAC is manufactured by Advantech Co. Ltd., Taiwan (model PCL-714). The experiment data collected are shown in the following Example 1.

Figure 3:
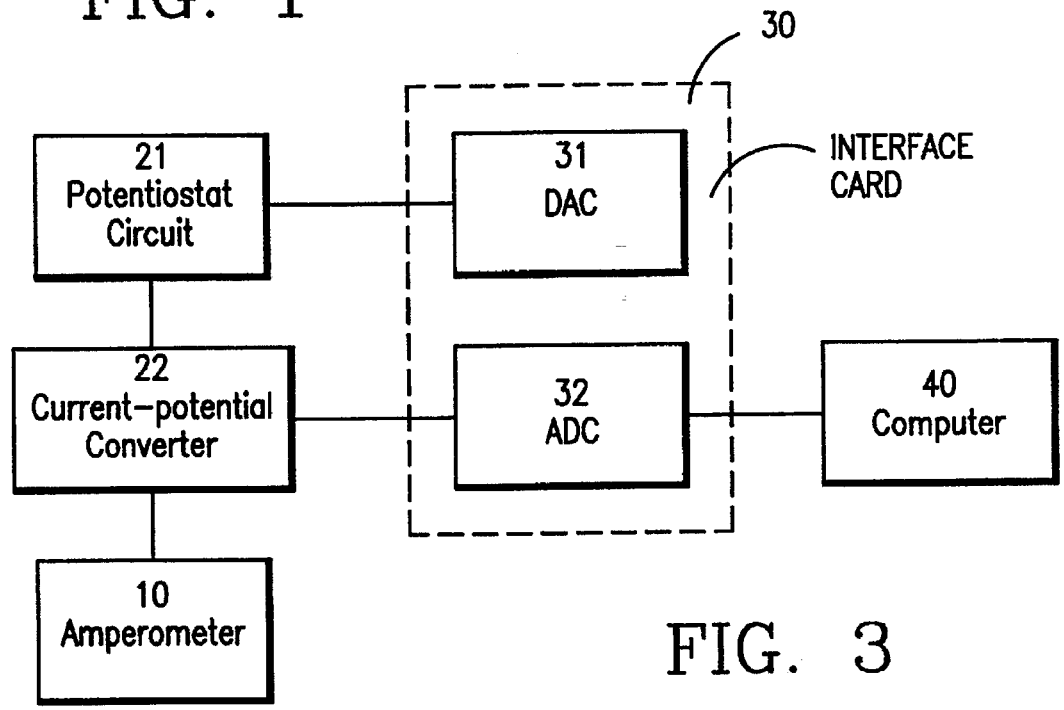
FIG. 3 is a block diagram which shows a system for collecting chemical signals from a chemical sensor according to a second preferred embodiment of the present invention.

FIG. 3 is a block diagram which shows a system for collecting chemical signals from a chemical sensor according to a second preferred embodiment of the present invention, in which 10 stands for the chemical sensor used in an amperometer, 21 stands for a potentiostat circuit, 22 stands for a current-potential converter, 30 stands for an interface card, 31 stands for DAC in the interface card, 32 stands for ADC in the interface card, and 40 stands for a computer. DAC 31 gives a specific electric potential to the potentiostat circuit 21 to cause the chemical sensor 10 to execute a potentiostat, cyclic voltammetry or square wave voltammetry to the operation. The current formed in the chemical sensor 10 is converted into voltage signals by current-potential converter 22, and then the voltage signals are measured by ADC 32. This system can be used in voltammetry operations such as polarography.

Figure 4:
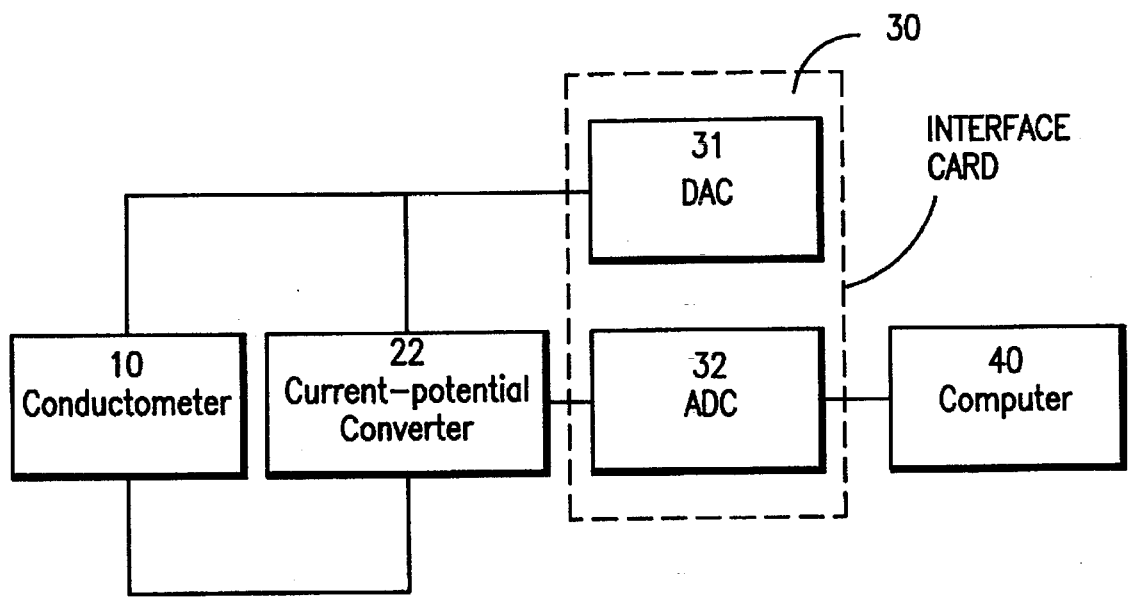
FIG. 4 is a block diagram which shows a system for collecting chemical signals from a chemical sensor according to a third preferred embodiment of the present invention.

FIG. 4 is a block diagram which shows a system for collecting chemical signals from a chemical sensor according to a third preferred embodiment of the present invention, in which the numbers 22, 30, 31, 32 and 40 represent the same elements represented by the like numbers in FIG. 3, and 10 represents a chemical sensor for conductometry. DAC 31 causes chemical sensor 10 to execute sine wave voltammetry. The resultant current, is, by means of the current-potential converter 22, converted to resistance signals, which are then measured by ADC 32. This system can be used in conductometry.

EXAMPLE 1

Figure 6:
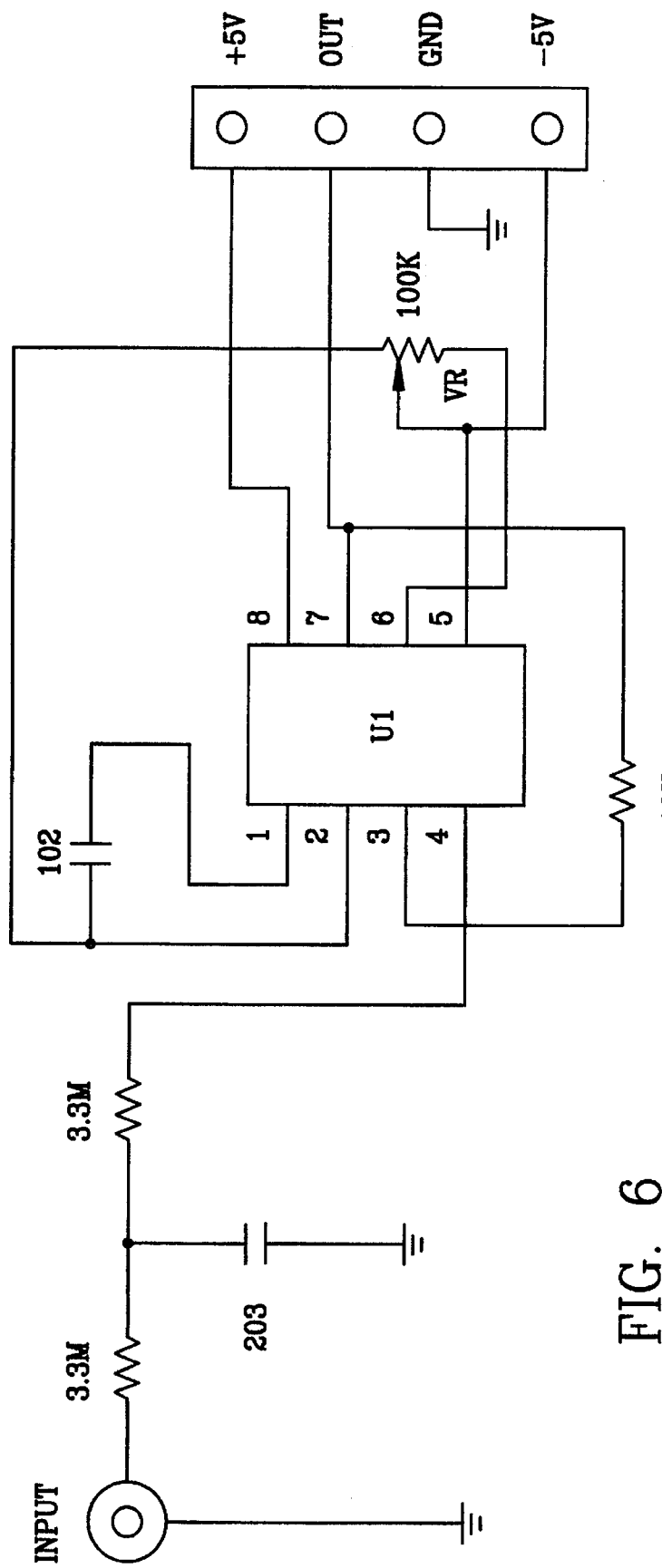
FIG. 6 is an electric circuit of an voltage follower, wherein an IC U1 is sold by Jujitsu Co., Japan under a code of OP41, F J9201.

The system shown in FIG. 1 was used to measure pH value of an aqueous buffer solution prepared by mixing 1:1 (v/v) of 0.1M acetic acid solution and 0.1M sodium acetate solution. A pH electrode Model PHM82 purchased from Radiometer, Denmark, was used as the chemical sensor 10; the circuit shown in FIG. 6 was used as the voltage follower 20; an IBM compatible AT computer was used as the computer 40; and a PCL-714 ADC/DAC interface card purchased from Advantech Co. Ltd., Taiwan was used as the ADC 30 in FIG. 1. 174 average pH values were obtained, each of which was obtained by recording about 30 thousand measurements (1–2 seconds measuring time) and calculating the average value of the about 30 thousand measurements. The results are shown as follows:

| Average pH | Appearing times | Accumulation of appearing times |
|---|---|---|
| 4.6287 | 2 | 2 |
| 4.6288 | 17 | 19 (2 + 7) |
| 4.6289 | 22 | 41 (19 + 22) |
| 4.6290 | 54 | 95 (41 + 54) |
| 4.6291 | 41 | 136 (95 + 41) |
| 4.6292 | 23 | 159 (136 + 23) |
| 4.6293 | 12 | 171 (159 + 12) |
| 4.6294 | 1 | 172 (171 + 1) |
| 4.6295 | 2 | 174 (172 + 2) |

Figure 5:
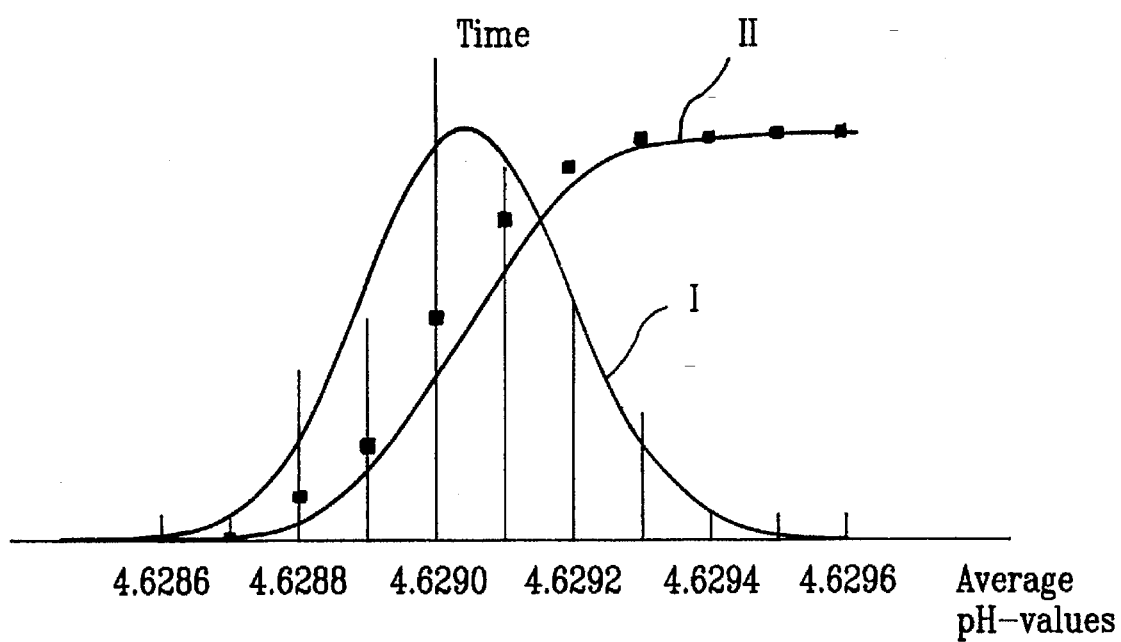
FIG. 5 is a plot which shows a pH value distribution of acetic acid/sodium acetate buffer solution measured by using the system in FIG. 1 and the algorithm in FIG. 2.

Two curves (normal distribution and accumulation distribution) were made according to the above data, as shown in FIG. 5. In FIG. 5, the horizontal axis stands for the average pH values. The vertical line at each average pH value represents the number of times an average pH value appears; the * at each average pH value represents the accumulation of the appearing times of the average pH values less than or equal to the average pH value. It can be seen from FIG. 5 that the distribution of experimental data fits the theoretical distribution represented by curves I and II. The standard deviation is 0.0002.

What is claimed is:

1. A method of using a computer to collect chemical signals directly from a chemical sensor used in amperometry or conductometry, comprising the steps of:

supplying an analog output of the chemical amperometry or conductometry sensor to a current-potential converter and potentiostat circuit in order to transform the analog output of the chemical sensor into a processed analog signal in preparation for analog-to-digital conversion in cooperation with a control program executed by the computer;

supplying an output of the current-potential converter and potentiostat circuit to an analog-to-digital converter in order to transform the processed analog signal into a digital signal; and transferring the digital signal output by the analog-to-digital converter to a computer, wherein the analog-to-digital converter further includes a digital-to-analog converter, and further comprising the steps of transferring digital signals from said computer to the digital-to-analog converter in order to convert the digital signals to analog signals, said supplying the converted digital signals to the potentiostat circuit for use in amperometry, the converted digital signals providing a specific electric potential to the potentiostat circuit to cause the chemical sensor to execute a potentiostat, cyclic voltammetry or square wave voltammetry operation.

2. A method of using a computer to collect chemical signals directly from a chemical sensor used in amperometry or conductometry, comprising the steps of:

supplying an analog output of the chemical amperometry or conductometry sensor to a current-potential converter and potentiostat circuit in order to transform the analog output of the chemical sensor into a processed analog signal in preparation for analog-to-digital conversion in cooperation with a control program executed by the computer;

supplying an output of the current-potential converter and potentiostat circuit to an analog-to-digital converter in order to transform the processed analog signal into a digital signal; and transferring the digital signal output by the analog-to-digital converter to a computer, wherein said analog-to-digital converter further includes a digital-to-analog converter, and further comprising the steps of transferring digital signals from said computer to the digital-to-analog converter in order to convert said digital signals to analog signals, and supplying the converted digital signals to said conductometer and current-potential converter for use in conductometry, the converted digital signals causing the chemical sensor to execute sine wave voltammetry.

3. A system for using a computer to collect chemical signals, comprising:

a computer;

a chemical sensor used in amperometry or conductometry;

a current-potential converter;

a potentiostat circuit;

means for supplying an analog output of the chemical amperometry of conductometry sensor to a current-potential converter and potentiostat circuit in order to transform the analog output of the chemical sensor into a processed analog signal in preparation for analog-to-digital conversion in cooperation with a control program executed by the computer;

an analog-to-digital converter;

means for supplying an output of the current-potential converter and potentiostat circuit to the analog-to-digital converter in order to transform the processed analog signal into a digital signal; and means for transferring the digital signal output by the analog-to-digital converter to the computer for analysis, wherein the analog-to-digital converter further includes a digital-to-analog converter, and further comprising means for transferring digital signals from said computer to said digital-to-analog converter in order to convert said digital signals to analog signals, and means for supplying said converted digital signals to said potentiostat circuit for use in amperometry, said converted digital signals providing a specific electric potential to the potentiostat circuit to cause the chemical sensor to execute a potentiostat, cyclic voltammetry or square wave voltammetry operation.

4. A system for using a computer to collect chemical signals, comprising:

a computer;

a chemical sensor used in amperometry or conductometry;

a current-potential converter;

a potentiostat circuit;

means for supplying an analog output of the chemical amperometry of conductometry sensor to a current-potential converter and potentiostat circuit in order to transform the analog output of the chemical sensor into a processed analog signal in preparation for analog-to-digital conversion in cooperation with a control program executed by the computer;

an analog-to-digital converter;

means for supplying an output of the current-potential converter and potentiostat circuit to the analog-to-digital converter in order to transform the processed analog signal into a digital signal; and means for transferring the digital signal output by the analog-to-digital converter to the computer for analysis, wherein the analog-to-digital converter further includes a digital-to-analog converter, and further comprising means for transferring digital signals from said computer to said digital-to-analog converter in order to convert said digital signals to analog signals, and means for supplying the converted digital signals to said conductometer and current-potential converter for use in conductometry, said converted digital signals causing the chemical sensor to execute sine wave voltammetry.

* * * * *